United States Patent
Bourgeois et al.

(10) Patent No.: US 9,702,486 B2
(45) Date of Patent: Jul. 11, 2017

(54) POLYURETHANE-POLYETHYLENE DELAMINATION RESISTANT TUBING WITH GAS BARRIER PROPERTIES

(75) Inventors: Philip Bourgeois, Perrysburg, OH (US); Munish Shah, Sylvania, OH (US)

(73) Assignee: Tekni-Plex, Inc., Wayne, PA (US)

( * ) Notice: Subject to any disclaimer, the term of this patent is extended or adjusted under 35 U.S.C. 154(b) by 909 days.

(21) Appl. No.: 13/586,288

(22) Filed: Aug. 15, 2012

(65) Prior Publication Data

US 2013/0190723 A1 Jul. 25, 2013

Related U.S. Application Data

(63) Continuation-in-part of application No. 13/354,029, filed on Jan. 19, 2012.

(51) Int. Cl.
*A61M 25/00* (2006.01)
*F16L 9/12* (2006.01)
(Continued)

(52) U.S. Cl.
CPC .............. *F16L 9/121* (2013.01); *A61L 29/041* (2013.01); *A61L 29/06* (2013.01); *A61L 29/085* (2013.01); *A61L 29/14* (2013.01); *A61M 39/08* (2013.01); *B32B 1/08* (2013.01); *B32B 7/12* (2013.01); *B32B 27/08* (2013.01); *B32B 27/308* (2013.01); *B32B 27/40* (2013.01); *F16L 11/04* (2013.01); *A61L 2420/08* (2013.01); *B32B 2250/03* (2013.01); *B32B 2250/24* (2013.01); *B32B 2250/40* (2013.01); *B32B 2274/00* (2013.01); *B32B 2307/412* (2013.01); *B32B 2307/51* (2013.01); *B32B 2535/00* (2013.01); *B32B 2597/00* (2013.01); *Y10T 137/0318* (2015.04)

(58) Field of Classification Search
CPC ................................................. A61M 25/0045
USPC .......................................................... 604/523
See application file for complete search history.

(56) References Cited

U.S. PATENT DOCUMENTS 4,211,741 A  7/1980  Ostoich
4,627,844 A  12/1986  Schmitt et al.
(Continued)

FOREIGN PATENT DOCUMENTS

DE  202004000533 U1  3/2004
EP      0244960 A1  11/1987
(Continued)

OTHER PUBLICATIONS

International Search Report and Written Opinion mailed Sep. 27, 2013 in Application No. PCT/US2013/049097.
(Continued)

*Primary Examiner* — Edelmira Bosques
(74) *Attorney, Agent, or Firm* — Polsinelli PC

(57) ABSTRACT

A tube comprising an inner layer, an outer layer and a barrier layer disposed between the inner layer and the outer layer, wherein the barrier layer is bound to the outer layer by a layer of adhesive disposed between the outer layer and the barrier layer and the barrier layer is bound to the inner layer by a layer of adhesive disposed between the inner layer and the barrier layer, wherein the inner layer comprises a polyethylene, the outer layer comprises a thermoplastic polyurethane and the barrier layer comprises a material that acts as a barrier to gas.

30 Claims, 1 Drawing Sheet

(51) Int. Cl.

| | | |
|---|---|---|
| *A61M 39/08* | (2006.01) | |
| *B32B 1/08* | (2006.01) | |
| *B32B 7/12* | (2006.01) | |
| *B32B 27/08* | (2006.01) | |
| *A61L 29/04* | (2006.01) | |
| *A61L 29/06* | (2006.01) | |
| *A61L 29/08* | (2006.01) | |
| *A61L 29/14* | (2006.01) | |
| *B32B 27/30* | (2006.01) | |
| *B32B 27/40* | (2006.01) | |
| *F16L 11/04* | (2006.01) | |

(56) References Cited

U.S. PATENT DOCUMENTS

| | | | | |
|---|---|---|---|---|
| 4,948,643 | A | | 8/1990 | Mueller |
| 5,052,444 | A | * | 10/1991 | Messerly et al. ............ 138/125 |
| 5,570,711 | A | | 11/1996 | Walsh |
| 5,733,619 | A | | 3/1998 | Patel et al. |
| 6,165,166 | A | | 12/2000 | Samuelson et al. |
| 6,230,749 | B1 | | 5/2001 | Kertesz |
| 6,357,485 | B2 | * | 3/2002 | Quigley et al. ............ 138/125 |
| 7,647,949 | B2 | | 1/2010 | Donohue et al. |
| 8,399,077 | B1 | * | 3/2013 | Bekele ...................... 428/35.2 |
| 2002/0061377 | A1 | | 5/2002 | Ketesz |
| 2002/0139428 | A1 | | 10/2002 | Ketesz |
| 2002/0144744 | A1 | | 10/2002 | Ketesz |
| 2003/0208259 | A1 | * | 11/2003 | Penhasi ....................... 623/1.15 |
| 2007/0119511 | A1 | | 5/2007 | Donohue et al. |
| 2007/0178131 | A1 | * | 8/2007 | Yamada et al. ............ 424/423 |
| 2009/0087606 | A1 | | 4/2009 | Julien |
| 2009/0286028 | A1 | | 11/2009 | Garver |
| 2009/0317611 | A1 | * | 12/2009 | Mueller et al. ............ 428/212 |

FOREIGN PATENT DOCUMENTS

| | | |
|---|---|---|
| EP | 1 208 969 A2 | 11/2000 |
| EP | 1 245 377 A1 | 3/2001 |
| EP | 1 249 336 A2 | 1/2002 |
| EP | 1 468 218 B1 | 1/2003 |
| EP | 2177805 A2 * | 4/2010 ............ F16L 11/04 |
| EP | 1468218 B1 | 6/2012 |
| JP | H10-305093 A | 11/1998 |
| WO | WO 9741906 A1 | 11/1997 |
| WO | WO 00/13896 A1 | 3/2000 |
| WO | WO 03/064909 A1 | 8/2003 |
| WO | WO03064909 A1 | 8/2003 |
| WO | WO 2005/068887 A1 | 1/2005 |

OTHER PUBLICATIONS

International Search Report and Written Opinion mailed Sep. 27, 2013 in Application No. PCT/US2013/055075.

Mar. 27, 2017 EPO minutes of oral proceedings with allowed EP claims 1-12 in EP13753469.9.

Office Action dated Jan. 25, 2016 in corresponding application JP2015-527625, with English translation.

International Preliminary Report on Patentability mailed Sep. 17, 2014 in International Patent Application No. PCT/US2013/055075.

Office Action issued Dec. 5, 2016 in corresponding Chinese Application No. 201380043388.7.

International Preliminary Report on Patentability mailed Sep. 22, 2014 in International Patent Application No. PCT/US2013/049097.

First Office Action dated May 4, 2016 in corresponding Chinese Application No. 201380043388.7 with English translation.

* cited by examiner

POLYURETHANE-POLYETHYLENE DELAMINATION RESISTANT TUBING WITH GAS BARRIER PROPERTIES

RELATED APPLICATIONS

This application is a continuation-in-part of and claims the benefit of priority of U.S. application Ser. No. 13/354,029 filed Jan. 19, 2012.

FIELD OF THE INVENTION

The present invention relates to polymeric tubing typically formed by a co-extrusion process, the tubing having multiple layers of the same or different polymeric materials, each layer successively adhered to each other.

BACKGROUND

Tubing comprised of polymeric material is used in many industrial and commercial applications including in the medical field. Various FDA compliant plastics are used, depending upon properties desired and the intended applications. Where the tubing is used to transport fluids for in vivo treatment of human patients, selection of the polymeric materials can be a factor.

Polyvinyl chloride (PVC) is one of the most widely used plastics. While structurally stable and easily formable into desired shapes, PVC is typically manufactured using plasticizers which can migrate out of the PVC matrix into bodily fluids and has other properties not ideally suited for medical treatment applications. Likewise, due to the inherent nature of plasticized PVC tubing, there arises the potential absorption of medicines and other components of aqueous fluids used in medical treatments into the sidewall of the PVC tube. Polyurethane is potentially a substitute for PVC. However, dual layer tubing comprised of polyurethane and polyethylene suffers from the inability of the two layers to remain adhered to each other under low to moderate stress, strain or mechanical manipulation conditions as well as the inability to sufficiently impede migration of oxygen through the layers. U.S. Pat. No. 4,627,844 to Schmitt ("Schmitt"), the disclosure of which is incorporated herein by reference as if fully set forth, discloses a tri-layer tube which is embodied in a commercial product sold under the trademark "SUREPATH 151" by the Natvar Division of Tekni-Plex, Inc. As disclosed in Schmitt, an outer layer of PVC and an inner fluid-contact layer of low density polyethylene (LDPE) are co-extruded with an intermediate tie layer of ethylene vinyl acetate copolymer (EVA). However, while Schmitt greatly reduces the possibility for the migration of additives from the PVC to the fluid and absorption of components from the fluid to the PVC tubing by providing a LDPE fluid-contact layer, elimination of the PVC is preferred. Other tubing configurations are disclosed in U.S. Pat. No. 7,647,949, U.S. Pat. No. 4,211,741 and U.S. Patent Publication No. 2007/0119511, the disclosures of which are incorporated by reference as if fully set forth herein. Where medical tubing is concerned, preservation of the integrity of reagents contained in fluids being routed through the tubing can be a concern. Similarly, prevention of migration of components out of the fluids through the tubing can be an issue. In such applications, incorporation into the tubing of a layer of material comprised of a gas barrier material can be implemented for purposes of preventing migration of gases such as oxygen into the fluid thus preserving oxygen sensitive reagents in the fluid.

SUMMARY OF THE INVENTION

In accordance with the invention there is provided a tube comprising an inner layer, an outer layer and a barrier layer disposed between the inner layer and the outer layer, wherein the barrier layer is bound to the outer layer by a layer of adhesive disposed between the outer layer and the barrier layer and the barrier layer is bound to the inner layer by a layer of adhesive disposed between the inner layer and the barrier layer, wherein the inner layer comprises a polyethylene, the outer layer comprises a thermoplastic polyurethane and the barrier layer comprises a material that acts as a barrier to gas.

The barrier layer preferably comprises more than about 90% by weight of an ethylene vinyl alcohol copolymer or a polyamide or blends thereof.

The adhesive typically comprises one or more ethylene acrylic copolymers, more typically one or more anhydride grafted ethylene acrylate copolymers and preferably one or more anhydride grafted ethylene methyl acrylate copolymers.

The inner layer typically comprises more than about 90% by weight of a polyethylene and the outer layer comprises more than about 90% by weight of an aromatic or aliphatic polyether based polyurethane.

The barrier layer typically comprises more than about 90% by weight of an ethylene vinyl alcohol copolymer or a polyamide or blends thereof and the adhesive comprises more than about 90% by weight of one or more ethylene acrylic copolymers, The barrier layer can comprise more than about 90% by weight of an ethylene vinyl alcohol copolymer or a polyamide or blends thereof and the inner layer can comprise more than about 90% by weight of a polyethylene and the outer layer can comprise more than about 90% by weight of an aromatic or aliphatic polyether based polyurethane.

The adhesive can comprise more than about 90% by weight of one or more ethylene acrylic copolymers and the inner layer can comprise more than about 90% by weight of a polyethylene and the outer layer can comprises more than about 90% by weight of an aromatic or aliphatic polyether based polyurethane.

The barrier layer can comprises more than about 90% by weight of an ethylene vinyl alcohol copolymer or a polyamide or blends thereof, the adhesive can comprise more than about 90% by weight of one or more ethylene acrylic copolymers, the inner layer can comprises more than about 90% by weight of a polyethylene and the outer layer can comprise more than about 90% by weight of an aromatic or aliphatic polyether based polyurethane.

The polyethylene typically comprises one or more of a low density polyethylene, a linear low density polyethylene and a high density polyethylene and the aromatic polyether based polyurethane can comprise a polytetramethyleneglycol-based polyurethane.

The adhesive can comprise more than about 90% by weight of one or more ethylene acrylic copolymers, the inner layer can comprise more than about 90% by weight of low density polyethylene (LDPE), the outer layer can comprise more than about 90% by weight of a polytetramethyleneglycol-based polyurethane and the middle layer can comprise more than about 90% of a material that acts as a barrier to gas.

The adhesive typically comprises more than about 90% by weight of one or more ethylene acrylic copolymers.

The thickness of the polyurethane outer layer is typically between about 0.001 inches (0.0254 mm) and about 0.025 inches (0.635 mm), the thickness of the inner polyethylene layer is typically between between about 0.001 inches (0.0254 mm) and about 0.025 inches (0.635 mm) and the thickness of the barrier layer is typically between about 0.001 inches (0.0254 mm) and about 0.025 inches (0.635 mm).

The inner and outer layers preferably do not visually delaminate when subjected to a stress and strain up to the tube's elastic yield point as measured in a mechanical tester at a pull rate of about 12 inches per minute at ambient conditions of 72 degrees F. (22° C.) and 50% relative humidity.

Preferably, the tube does not visually delaminate when submersed in water at 60° C. for 36 hours.

The tube preferably has a central axial fluid flow passage through which aqueous fluid is routed, the inner layer having a radially inner wall surface that contacts the aqueous fluid the outer and inner layers resisting delamination when subjected to a stress and strain up to the tube's elastic yield point as measured in a mechanical tester at a pull rate of about 12 inches per minute at ambient conditions of 72 degrees F. (22° C.) and 50% relative humidity. Such a tube preferably does not visually delaminate after being submersed in water at 60° C. for 36 hours.

In such a tube, the thickness of the adhesive disposed between the barrier layer and the outer layer is preferably between about 0.001 inches (0.0254 mm) and about 0.025 inches (0.635 mm) and the thickness of the adhesive disposed between the barrier layer and the inner layer is preferably between about 0.001 inches (0.0254 mm) and about 0.025 inches (0.635 mm)

In another aspect of the invention there is provided a medical tube for transport of aqueous fluid comprising:
an inner layer comprising more than about 90% by weight of a polyethylene,
an outer layer comprising more than about 90% by weight of a an aromatic polyether-based polyurethane,
a barrier layer disposed between the outer and inner layers comprising more than about 90% by weight of a material that acts as a barrier to gas, and,
an adhesive disposed between the barrier layer and the outer layer and disposed between the barrier layer and the inner layer, the adhesive comprising one or more ethylene acrylic copolymers, In such an embodiment, the inner and outer layers preferably do not visually delaminate when subjected to a stress and strain up to the tube's elastic yield point as measured in a mechanical tester at a pull rate of about 12 inches per minute at ambient conditions of 72 degrees F. (22° C.) and 50% relative humidity.

In such an embodiment, the tube preferably does not visually delaminate after being submersed in water at 60° C. for 36 hours.

In such an embodiment, the adhesive comprises one or more anhydride grafted ethylene acrylate copolymers.

In another aspect of the invention there is provided a medical tube for transport of an aqueous fluid comprising:
an inner layer comprised of at least about 90% by weight of a polyethylene.
an outer layer comprised of at least about 90% by weight of an aromatic polyether-based polyurethane,
a barrier layer disposed between the outer and inner layers comprising more than about 90% by weight of a material that acts as a barrier to gas, and,
an adhesive disposed between the barrier layer and the outer layer and disposed between the barrier layer and the inner layer, the adhesive comprising more than about 90% by weight of one or more ethylene acrylic copolymers,
wherein the tubing does not visually delaminate after being submersed in water at 60° C. for 36 hours.

In another aspect of the invention, there is provided a medical tube for transport of an aqueous fluid comprising:
an inner layer comprised of at least about 90% by weight of a low density polyethylene,
an outer layer comprised of at least about 90% by weight of a polytetramethyleneglycol-based polyurethane,
a barrier layer disposed between the outer and inner layers comprising more than about 90% by weight of a material that acts as a barrier to gas, and,
an adhesive disposed between the barrier layer and the outer layer and disposed between the barrier layer and the inner layer, the adhesive comprising one or more ethylene acrylic copolymers,
wherein the tubing does not visually delaminate when subjected to a stress and strain up to the tube's elastic yield point as measured in a mechanical tester at a pull rate of about 12 inches per minute at ambient conditions of 72 degrees F. (22° C.) and 50% relative humidity, and,
wherein the tubing does not visually delaminate after being submersed in water at 60° C. for 36 hours.

In another aspect of the invention there is provided, a method of forming a medical tube comprising an outer layer, an innermost layer and an intermediate layer disposed between the outer layer and the innermost layer, the method comprising:
selecting a first polymeric material having a selected structural stability;
selecting a second polymeric material that is inert to aqueous fluids;
selecting a third polymeric material that acts as a barrier to gas;
selecting a fourth polymeric material that readily bonds and adheres to the first and second polymeric materials on co-extrusion and cooling of the materials;
co-extruding the selected first, second, third and fourth polymeric materials to form the medical tubing in a configuration that has an outer layer comprising at least about 90% by weight of the first polymeric material, an inner layer comprising at least about 90% weight of the second polymeric material, a layer disposed between the inner and outer layers that comprises at least about 90% by weight of the third polymeric material, a layer of the fourth material disposed between the outer layer and the layer of the third polymeric material and a layer of the fourth material disposed between the inner layer and the layer of the third polymeric material.

In such a method, the first polymeric material is typically selected to be a polyurethane, the second polymeric material is selected to be a polyethylene, the third polymeric material is selected from the group consisting of an ethylyene vinyl alcohol copolymer and a polyamide and the fourth polymeric material is one or more ethylene acrylic copolymers, In such a method, the first polymeric material is preferably selected to be a polyurethane, the second polymeric material is selected to be a polyethylene, the third polymeric material is selected from the group consisting of an ethylyene vinyl alcohol copolymer and a polyamide and the fourth polymeric material is selected such that the medical tubing does not visually delaminate after being submersed in water at 60° C. for 36 hours.

In such a method, the adhesive typically comprises one or more anhydride grafted ethylene acrylate copolymers.

In another aspect of the invention there is provided, a method of delivering an aqueous fluid to a subject comprising;
selecting a tube comprising an inner layer, an outer layer and a barrier layer disposed between the inner and outer layers, wherein the inner layer comprises a polyethylene, the outer layer comprises a thermoplastic polyurethane and the barrier layer comprises one or more of an ethylene vinyl alcohol copolymer and a polyamide;
wherein the tube has a central fluid flow passage surrounded by the layers;
routing an aqueous fluid through the central fluid flow passage of the tube, and,
delivering the aqueous fluid routed through the central fluid flow passage into a blood vessel of the subject.
The step of selecting preferably comprises:
selecting the tube such that a layer of an adhesive is disposed between the outer layer and the barrier layer and between the inner layer and the barrier layer.
The step of selecting typically comprises:
co-extruding the outer, inner and barrier layers and adhesive layers to form the tube and selecting the adhesive to comprise more than about 90% by weight of one or more ethylene acrylic copolymers.
The adhesive typically comprises one or more anhydride grafted ethylene acrylate copolymers.
The adhesive can comprise one or more anhydride grafted ethylene methyl acrylate copolymers.

BRIEF DESCRIPTION OF THE DRAWINGS

The drawings depict one or more embodiments of the invention that are shown by way of examples of the invention wherein.

DETAILED DESCRIPTION

Figure 1:
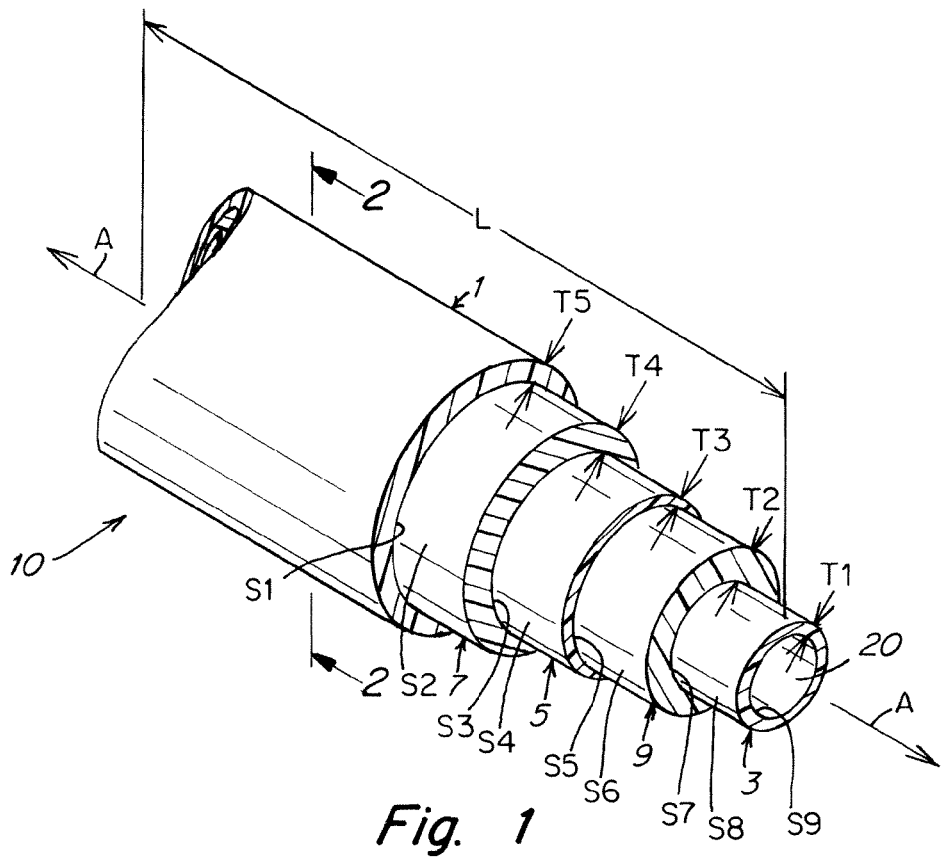
FIG. 1 is a schematic perspective view of a five-layered tube showing the outer and middle or intermediate layers broken away in order to better illustrate the construction and arrangement of the tubing.

There is shown in FIG. 1 an embodiment of a co-extruded five-layer tubing 10 according to the invention which comprises an outer layer 1 comprised of at least about 90% by weight of a polyurethane material, typically a polytetramethyleneglycol-based polyurethane one example of which is Lubrizol TPU Pellethane 2363-90AE, an inner fluid-contact layer 3 comprised of at least about 90% by weight of a polyethylene material, typically a low density polyethylene, one example of which is Westlake LDPE EM808AA, an intermediate gas barrier layer 5 comprised of at least about 90% by weight of an ethylene vinyl alcohol copolymer (EVOH), a polyamide or a mixture or blend of two or more thereof and bonding layers 7, 9 comprised of an adhesive material that bonds the barrier layer 5 to the outer 1 and inner 3 layers. The gas barrier layer 5 acts as a barrier to gases generally such as oxygen, nitrogen, hydrogen, chlorine, nitrous oxide and the like. The adhesive layers 7, 9 preferably comprise a material that renders the tubing 10 subsequent to extrusion resistant to delamination where the tubing does not visually delaminate after being subjected to submersion in water at 60° C. for 36 hours and subsequently mechanically flattened by manual squeezing of the tube from its normal round in cross-sectional condition to a flattened or oval shape cross-sectional shape or condition.

The adhesive material is most preferably selected to comprise one or more ethylene acrylic copolymers, an example of which is an anhydride grafted ethylene methyl acrylate copolymer, a specific example of which is an anhydride grafted ethylene methyl acrylate copolymer such as commercially available Westlake Tymax GA 7001 (Anhydride grafted Ethylene Methyl Acrylate Copolymer).

As shown in FIG. 1 the outer layer of polyurethane 1 has a radially inner facing surface S1 that binds and adheres to a radially outer facing surface S2 of the anhydride modified acrylate adhesive layer 7. The adhesive layer 7 has a radially inner facing surface S3 that binds to the radially outer facing surface S4 of the barrier layer 5. The barrier layer 5 has a radially inner facing surface S5 that binds to the radially outer facing surface S6 of another layer 9 of adhesive. The adhesive layer 9 has a radially inner facing surface S7 that binds to the radially outer facing surface S8 of the inner polyethylene layer 3. The intermediate barrier layer 5 adheres to the outer 1 and inner 3 layers such that the three layers 1, 3 and 5 remain adhered to layers 7, 9 and to each other when the tube 10 is subjected to a stress and strain up to the tube's elastic yield point as measured in a mechanical tester at a pull rate of about 12 inches per minute at ambient conditions of 72 degrees F. (22° C.) and 50% relative humidity. Mechanical testers for measuring such stress and strain are knowing in the art, an example of which is a Lloyd LR5K Plus mechanical tester. Elastic yield point is the highest point at which one or more of the layers of the tubing permanently deforms or as otherwise defined in "*Introduction to Physical Polymer Science, 4$^{th}$ Edition,*" L. H. Sperling (author), John Wiley & Sons (publisher), 2006, the disclosure of which is incorporated by reference in its entirety as if fully set forth herein.

The layers 1, 3, 5, 7, 9 of such tubing 10 remain adhered to each other such that the layers do not visually delaminate after being subjected to submersion in water at 60° C. for 36 hours and subsequently mechanically flattened by manual squeezing of the tube from its normal round in cross-sectional condition to a flattened or oval shape cross-sectional shape or condition.

Figure 2:
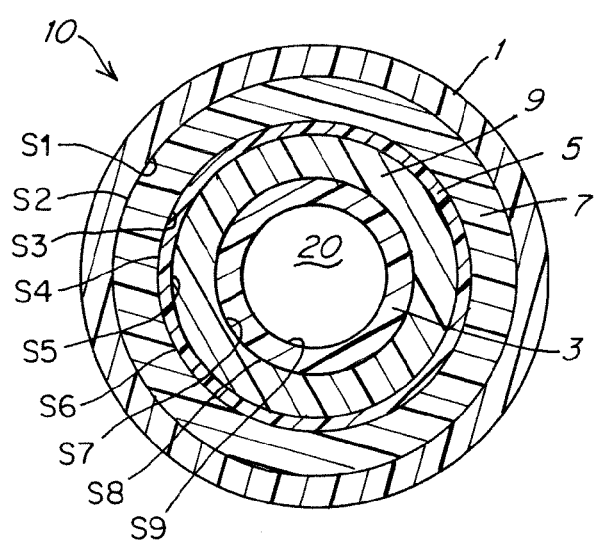
FIG. 2 is a cross-sectional view taken along lines 2-2 of the tube 10 shown in FIG. 1.

As shown in FIGS. 1 and 2, the layers 1, 3, 5 are formed into structurally stable walls that surround and enclose a central hollow fluid passage 20 through which an aqueous solution is routed and flows along an axial A direction contacting the radially inner facing surface S9 of the inner layer 3. The adhesive layers 7, 9 bind and hold the structural layers, inner 3, intermediate 5 and outer 1 together.

The inner layer 3 provides a radially inner fluid-contact surface S9, the thickness, of the inner layer 3 typically ranging in cross-sectional thickness T1 of between about 0.001 inches (0.0254 mm) and about 0.025 inches (0.635 mm). The intermediate layer 5 typically ranges in cross-sectional thickness T3 of between about 0.001 inches (0.0254 mm) and about 0.025 inches (0.635 mm). The outer layer 1 typically ranges in cross-sectional thickness T5 of between about 0.001 inches (0.0254 mm) and about 0.025 inches (0.635 mm). The adhesive layers 7, 9 typically range in cross-sectional thickness T2, T4 of between about 0.001 inches (0.0254 mm) and about 0.025 inches (0.635 mm).

The polyethylene material is preferably a branched low-density polyethylene (LDPE), such as Westlake EM808, available from Westlake Chemical Corporation. The polyethylene material can be a linear low density polyethylene (LLDPE) such as Dowlex 2035G, available from the Dow Chemical Company. The polyethylene material can also be a high-density polyethylene (HDPE), such as Chevron 9506 HDPE, Chevron 9406 HDPE, and Chevron 9503 HDPE, available from Chevron Corporation. The polyethylene material can be a mixture or blend of two or more of the aforementioned polyethylene materials.

The polyurethane elastomer (TPU) is typically the reaction product of a polyol and isocyanate and usually includes a combination of hard and soft segment domains. An aromatic polyether-based TPU or an aliphatic polyether-based TPU can be used such as a polytetramethyleneglycol-based polyurethane. Such examples of these TPU's include the Pellethane 2363-90 AE series available from the Lubrizol Corporation.

The respective thickness of each layer of tubing 10 can be controlled by conventional multi-layer extrusion tooling and equipment and typically includes a die set configured for producing multi-layer tubing such as a five-layer tube as shown in FIG. 1. Such a suitable extrusion apparatus is selected so as to provide a uniform thickness of the layers 1, 3, 5, 7, 9 along the substantial entirety of the axial length L of all of the layers 1, 3, 5, 7, 9.

The polymeric materials of which the layers 1, 3, 5, 7, 9 are comprised are preferably selected so as to be manually flexible along and around the axis A of the tubing. The polymeric materials are also selected so as to maintain the integrity of the tubing 10 (namely delamination does not occur) and its transparency or clarity after being subjected to ethylene oxide (EtO) and gamma irradiation sterilization processes.

The foregoing description is intended to illustrate and not limit the scope of the invention, those skilled in the art will realize that equivalents thereof are contemplated by the description above and that changes and modifications may be made thereto without departing from the spirit of the invention, all such equivalents, changes and modifications falling within the scope of the claims hereof.

The invention claimed is:

1. A tube comprising an inner layer, an outer layer and a barrier layer disposed between the inner layer and the outer layer, wherein the barrier layer is bound to the outer layer by a layer of adhesive disposed between the outer layer and the barrier layer and the barrier layer is bound to the inner layer by a layer of adhesive disposed between the inner layer and the barrier layer, wherein the inner layer comprises a polyethylene, the outer layer comprises a thermoplastic polyurethane and the barrier layer comprises a material that acts as a barrier to gas.

2. The tube of claim 1 wherein the barrier layer comprises more than about 90% by weight of an ethylene vinyl alcohol copolymer or a polyamide or blends thereof.

3. The tube of claim 1 wherein the adhesive comprises one or more ethylene acrylic copolymers.

4. The tube of claim 3 wherein the adhesive comprises one or more anhydride grafted ethylene acrylate copolymers.

5. The tube of claim 4 wherein the adhesive comprises one or more anhydride grafted ethylene methyl acrylate copolymers.

6. The tube of claim 1 where the inner layer comprises more than about 90% by weight of a polyethylene and the outer layer comprises more than about 90% by weight of an aromatic or aliphatic polyether based polyurethane.

7. The tube of claim 1 wherein the barrier layer comprises more than about 90% by weight of an ethylene vinyl alcohol copolymer or a polyamide or blends thereof and the adhesive comprises more than about 90% by weight of one or more ethylene acrylic copolymers.

8. The tube of claim 1 wherein the barrier layer comprises more than about 90% by weight of an ethylene vinyl alcohol copolymer or a polyamide or blends thereof and the inner layer comprises more than about 90% by weight of a polyethylene and the outer layer comprises more than about 90% by weight of an aromatic or aliphatic polyether based polyurethane.

9. The tube of claim 1 wherein the adhesive comprises more than about 90% by weight of one or more ethylene acrylic copolymers and the inner layer comprises more than about 90% by weight of a polyethylene and the outer layer comprises more than about 90% by weight of an aromatic or aliphatic polyether based polyurethane.

10. The tube of claim 1 wherein the barrier layer comprises more than about 90% by weight of an ethylene vinyl alcohol copolymer or a polyamide or blends thereof, the adhesive comprises more than about 90% by weight of one or more ethylene acrylic copolymers, the inner layer comprises more than about 90% by weight of a polyethylene and the outer layer comprises more than about 90% by weight of an aromatic or aliphatic polyether based polyurethane.

11. The tube of claim 1 where the polyethylene comprises one or more of a low density polyethylene, a linear low density polyethylene and a high density polyethylene and wherein the aromatic polyether based polyurethane comprises a polytetramethyleneglycol-based polyurethane.

12. The tube of claim 1 where the adhesive comprises more than about 90% by weight of one or more ethylene acrylic copolymers, the inner layer comprises more than about 90% by weight of low density polyethylene (LDPE), the outer layer comprises more than about 90% by weight of a polytetramethyleneglycol-based polyurethane and the barrier layer comprises more than about 90% of a material that acts as a barrier to gas.

13. The tube of claim 3 wherein the adhesive comprises more than about 90% by weight of one or more ethylene acrylic copolymers.

14. The tube of claim 1 wherein the thickness of the polyurethane outer layer is between about 0.001 inches (0.0354 mm) and about 0.025 inches (0.635 mm), the thickness of the inner polyethylene layer is between about 0.001 inches (0.0354 mm) and about 0.025 inches (0.635 mm) and the thickness of the barrier layer is between about 0.001 inches (0.0354 mm) and about 0.025 inches (0.635 mm).

15. The tube of claim 1 wherein the inner and outer layers do not visually delaminate when subjected to a stress and strain up to the tube's elastic yield point as measured in a mechanical tester at a pull rate of about 12 inches per minute at ambient conditions of 72 degrees F. (22° C.) and 50% relative humidity.

16. The tube of claim 1 wherein the tube does not visually delaminate when submersed in water at 60° C. for 36 hours.

17. The tube of claim 1 wherein the tube has a central axial fluid flow passage through which aqueous fluid is routed, the inner layer having a radially inner wall surface that contacts the aqueous fluid, and the outer and inner layers resisting delamination when subjected to a stress and strain up to the tube's elastic yield point as measured in a mechanical tester at a pull rate of about 12 inches per minute at ambient conditions of 72 degrees F. (22° C.) and 50% relative humidity.

18. The tube of claim 10 wherein the tube does not visually delaminate after being submersed in water at 60° C. for 36 hours.

19. The tube of claim 12 wherein thickness of the adhesive disposed between the barrier layer and the outer layer is between about 0.001 inches (0.0354 mm) and about 0.025 inches (0.635 mm) and wherein the thickness of the adhesive disposed between the barrier layer and the inner layer is between about 0.001 inches (0.0354 mm) and about 0.025 inches (0.635 mm).

20. A medical tube for transport of aqueous fluid comprising:
   an inner layer comprising more than about 90% by weight of a polyethylene,
   an outer layer comprising more than about 90% by weight of an aromatic polyether-based polyurethane,
   a barrier layer disposed between the outer and inner layers comprising more than about 90% by weight of a material that acts as a barrier to gas, and,
   an adhesive disposed between and binding the barrier layer and the outer layer and disposed between and binding the barrier layer and the inner layer, the adhesive comprising one or more ethylene acrylic copolymers.

21. The medical tube of claim 20 wherein the inner and outer layers do not visually delaminate when subjected to a stress and strain up to the tube's elastic yield point as measured in a mechanical tester at a pull rate of about 12 inches per minute at ambient conditions of 72 degrees F. (22° C.) and 50% relative humidity.

22. The tube of claim 20 wherein the tube does not visually delaminate after being submersed in water at 60° C. for 36 hours.

23. The tube of claim 20 wherein the adhesive comprises one or more anhydride grafted ethylene acrylate copolymers.

24. A medical tube for transport of an aqueous fluid comprising:
   an inner layer comprised of at least about 90% by weight of a polyethylene,
   an outer layer comprised of at least about 90% by weight of an aromatic polyether-based polyurethane,
   a barrier layer disposed between the outer and inner layers comprising more than about 90% by weight of a material that acts as a barrier to gas,
   an adhesive disposed between and binding the barrier layer and the outer layer and disposed between and binding the barrier layer and the inner layer, the adhesive comprising more than about 90% by weight of one or more ethylene acrylic copolymers, and
   wherein said tubing does not visually delaminate after being submersed in water at 60° C. for 36 hours.

25. A medical tube for transport of an aqueous fluid comprising:
   an inner layer comprised of at least about 90% by weight of a low density polyethylene,
   an outer layer comprised of at least about 90% by weight of a polytetramethyleneglycol-based polyurethane,
   a barrier layer disposed between the outer and inner layers comprising more than about 90% by weight of a material that acts as a barrier to gas, and,
   an adhesive disposed between and binding the barrier layer and the outer layer and disposed between and binding the barrier layer and the inner layer, the adhesive comprising one or more ethylene acrylic copolymers,
   wherein the tubing does not visually delaminate when subjected to a stress and strain up to the tube's elastic yield point as measured in a mechanical tester at a pull rate of about 12 inches per minute at ambient conditions of 72 degrees F. (22° C.) and 50% relative humidity, and,
   wherein the tubing does not visually delaminate after being submersed in water at 60° C. for 36 hours.

26. Method of delivering an aqueous fluid to a subject comprising;
   selecting a tube comprising an inner layer, an outer layer, a barrier layer disposed between the inner and outer layers, an adhesive layer disposed between and binding the inner and barrier layers and an adhesive layer disposed between and binding the outer and barrier layers,
   wherein the inner layer comprises a polyethylene, the outer layer comprises a thermoplastic polyurethane and the barrier layer comprises one or more of an ethylene vinyl alcohol copolymer and a polyamide;
   wherein the tube has a central fluid flow passage surrounded by the layers;
   routing an aqueous fluid through the central fluid flow passage of the tube, and,
   delivering the aqueous fluid routed through the central fluid flow passage into a blood vessel of the subject.

27. The method of claim 26 wherein the step of selecting comprises:
   selecting the tube such that a layer of an adhesive is disposed between the outer layer and the barrier layer and between the inner layer and the barrier layer.

28. The method of claim 27 wherein the outer, inner and barrier layers and adhesive layers of the selected tube are co-extruded to form the tube and wherein the adhesive comprises more than about 90% by weight of one or more ethylene acrylic copolymers.

29. The method of claim 28 wherein the adhesive comprises one or more anhydride grafted ethylene acrylate copolymers.

30. The method of claim 29 wherein the adhesive comprises one or more anhydride grafted ethylene methyl acrylate copolymers.

* * * * *